| | | US007087040B2 |

(12) United States Patent
McGuckin, Jr. et al.

(10) Patent No.: US 7,087,040 B2
(45) Date of Patent: Aug. 8, 2006

(54) APPARATUS FOR DELIVERING ABLATION FLUID TO TREAT LESIONS

(75) Inventors: James F. McGuckin, Jr., Radnor, PA (US); Stephan A. DeFonzo, Wayne, PA (US)

(73) Assignee: Rex Medical, L.P., Conshohocken, PA (US)

( * ) Notice: Subject to any disclaimer, the term of this patent is extended or adjusted under 35 U.S.C. 154(b) by 79 days.

(21) Appl. No.: 10/074,468

(22) Filed: Feb. 12, 2002

(65) Prior Publication Data
US 2002/0120238 A1 Aug. 29, 2002

Related U.S. Application Data

(60) Provisional application No. 60/272,119, filed on Feb. 28, 2001.

(51) Int. Cl.
*A61M 5/178* (2006.01)
*A61M 5/32* (2006.01)

(52) U.S. Cl. .................. 604/158; 604/164.12; 604/159; 604/164.01; 604/272

(58) Field of Classification Search ......... 604/158–159, 604/164.01–164.12, 272, 173, 264, 128, 604/509, 103.02, 511, 532, 95.01, 727, 170.03, 604/515, 163, 165.01, 165.02, 165.04, 166.01; 606/198

See application file for complete search history.

(56) References Cited

U.S. PATENT DOCUMENTS

| 4,013,080 A | 3/1977 | Froning |
| RE31,873 E | 4/1985 | Howes |
| 4,645,491 A | 2/1987 | Evans |
| 4,760,847 A | 8/1988 | Vaillancourt |
| 4,808,157 A | 2/1989 | Coombs |
| 4,842,585 A | 6/1989 | Witt |
| 4,846,799 A | 7/1989 | Tanaka et al. |
| 4,869,259 A | 9/1989 | Elkins |
| 4,926,860 A | 5/1990 | Stice et al. |
| 4,958,901 A | 9/1990 | Coombs |

(Continued)

FOREIGN PATENT DOCUMENTS

WO      WO 9846119      10/1998

OTHER PUBLICATIONS

Second Department of Internal Medicine, Faculty of Medicine, University of Tokyo, Japan, Gastroenterologia Japonica (Japan) Feb. 1991, p. 47–50, "Multiple–needle insertion method in percutaneous ethanol injection therapy for liver neoplasms", Shiina S; Heta Y; Niwa Y; Komatsu Y; Tanaka T; Yoshiura K; Hamada E; Ohshima M; Mutoh H; Kurita M; et al.

T. G. Frank, W. Xu and A. Cuschieri, "Instruments based on shape–memory alloy properties for minimal access surgery, interventional radiology and flexible endoscopy", 2000 (4 pages).

*Primary Examiner*—Kevin C. Sirmons
*Assistant Examiner*—Andrew Gilbert
(74) *Attorney, Agent, or Firm*—Neil D. Gershon

(57) ABSTRACT

A surgical apparatus for delivering fluid to treat a lesion comprising a housing, an elongated member extending from the housing, and a plurality of tines positioned in the housing. Each of the tines has a lumen and at least one opening communicating with the lumen for delivering fluid to the lesion. An actuator is operatively associated with the tines and actuable to a first position to move the plurality of tines from a retracted position substantially within the elongated member to a first deployed position extending from the elongated member and actuable to a second position to move the plurality of tines from the first position to a second deployed position.

10 Claims, 15 Drawing Sheets

U.S. PATENT DOCUMENTS

| | | |
|---|---|---|
| 5,067,957 A | 11/1991 | Jervis |
| 5,102,396 A | 4/1992 | Bommarito |
| 5,139,485 A | 8/1992 | Smith et al. |
| 5,160,323 A | 11/1992 | Andrew |
| 5,195,526 A | 3/1993 | Michelson |
| 5,207,652 A | 5/1993 | Kay |
| 5,215,527 A | 6/1993 | Beck et al. |
| 5,231,989 A | 8/1993 | Middleman et al. |
| 5,236,424 A | 8/1993 | Imran |
| 5,242,448 A | 9/1993 | Pettine et al. |
| 5,275,611 A | 1/1994 | Behl |
| 5,354,279 A | 10/1994 | Höfling |
| 5,360,416 A | 11/1994 | Ausherman et al. |
| 5,385,148 A | 1/1995 | Lesh et al. |
| 5,385,544 A | 1/1995 | Edwards et al. |
| 5,403,311 A | 4/1995 | Abele et al. |
| 5,405,376 A | 4/1995 | Mulier et al. |
| 5,419,777 A | 5/1995 | Hofling |
| 5,431,649 A | 7/1995 | Mulier et al. |
| 5,435,805 A | 7/1995 | Edwards et al. |
| 5,458,597 A | 10/1995 | Edwards et al. |
| 5,464,395 A | 11/1995 | Faxon et al. |
| 5,507,802 A | 4/1996 | Imran |
| 5,558,673 A | 9/1996 | Edwards et al. |
| 5,562,683 A | 10/1996 | Chan |
| 5,562,687 A | 10/1996 | Chan |
| 5,588,960 A | 12/1996 | Edwards et al. |
| 5,599,345 A | 2/1997 | Edwards et al. |
| 5,601,572 A | 2/1997 | Middleman et al. |
| 5,607,389 A | 3/1997 | Edwards et al. |
| 5,611,778 A | 3/1997 | Brinon |
| 5,672,174 A | 9/1997 | Gough et al. |
| 5,683,384 A | 11/1997 | Gough et al. |
| 5,693,029 A | 12/1997 | Leonhardt |
| 5,713,853 A | 2/1998 | Clark et al. |
| 5,738,650 A | 4/1998 | Gregg |
| 5,795,318 A | 8/1998 | Wang et al. |
| 5,810,804 A | 9/1998 | Gough et al. |
| 5,827,276 A | 10/1998 | LeVeen et al. |
| 5,849,011 A * | 12/1998 | Jones et al. .................. 606/47 |
| 5,855,576 A | 1/1999 | LeVeen et al. |
| 5,863,290 A | 1/1999 | Gough et al. |
| 5,873,865 A | 2/1999 | Horzewski et al. |
| 5,897,531 A | 4/1999 | Amirana |
| 5,964,796 A | 10/1999 | Imran |
| 5,980,517 A | 11/1999 | Gough |
| 6,004,295 A | 12/1999 | Langer et al. |
| 6,009,877 A | 1/2000 | Edwards |
| 6,059,780 A | 5/2000 | Gough et al. |
| 6,074,367 A | 6/2000 | Hubbell |
| 6,080,150 A | 6/2000 | Gough |
| 6,102,887 A | 8/2000 | Altman |
| 6,106,521 A | 8/2000 | Blewett et al. |
| 6,129,726 A | 10/2000 | Edwards et al. |
| 6,132,425 A | 10/2000 | Gough |
| 6,159,196 A | 12/2000 | Ruiz |
| 6,179,813 B1 | 1/2001 | Ballow et al. |
| 6,190,353 B1 | 2/2001 | Makower et al. |
| 6,190,360 B1 | 2/2001 | Iancea et al. |
| 6,200,274 B1 | 3/2001 | McNeirney |
| 6,203,524 B1 | 3/2001 | Burney et al. |
| 6,217,554 B1 | 4/2001 | Green |
| 6,217,559 B1 * | 4/2001 | Foster ........................ 604/195 |
| 6,221,049 B1 | 4/2001 | Selmon et al. |
| 6,228,049 B1 | 5/2001 | Schroeder et al. |
| 6,231,591 B1 * | 5/2001 | Desai ........................ 606/210 |
| 6,254,573 B1 | 7/2001 | Haim et al. |
| 6,280,424 B1 | 8/2001 | Chang et al. |
| 6,283,951 B1 | 9/2001 | Flaherty et al. |
| 6,302,870 B1 | 10/2001 | Jacobsen et al. |
| 6,306,141 B1 | 10/2001 | Jervis |
| 6,319,230 B1 | 11/2001 | Palasis et al. |
| 6,346,095 B1 | 2/2002 | Gross et al. |
| 6,425,887 B1 | 7/2002 | McGuckin et al. |
| 6,428,517 B1 | 8/2002 | Hochman et al. |
| 6,432,092 B1 * | 8/2002 | Miller ........................ 604/272 |
| 6,511,458 B1 | 1/2003 | Milo et al. |
| 6,730,061 B1 * | 5/2004 | Cuschieri et al. ............ 604/158 |

* cited by examiner

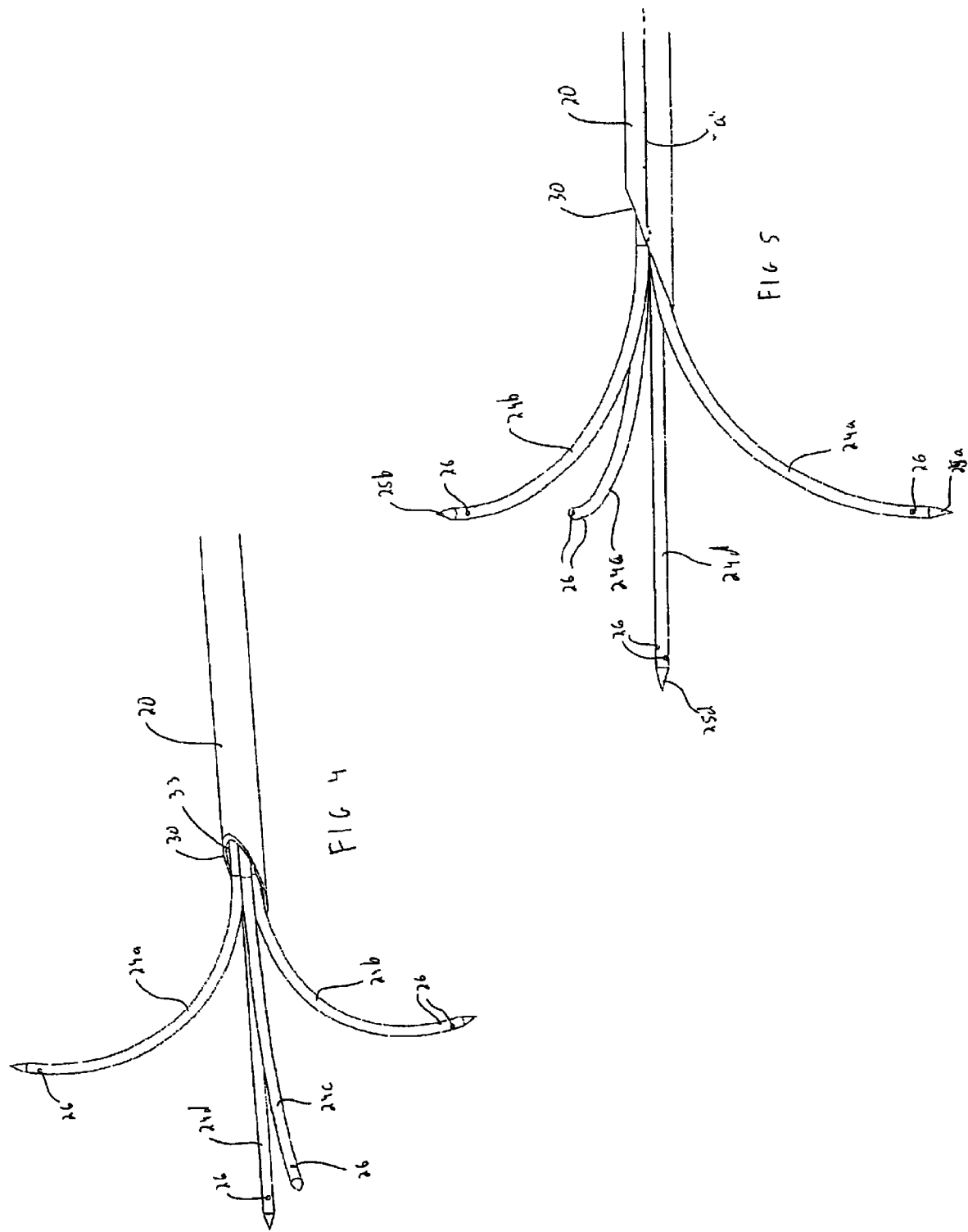

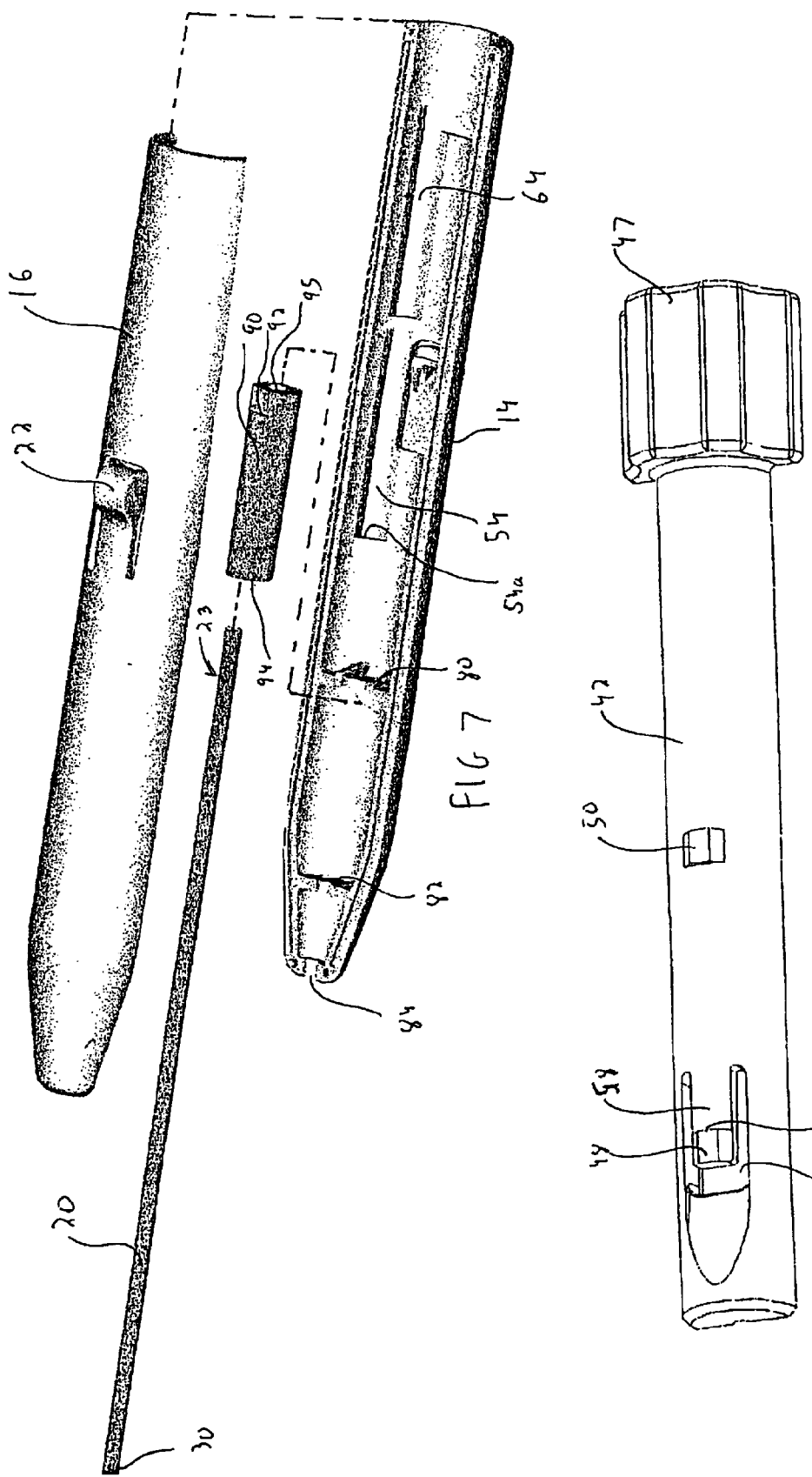

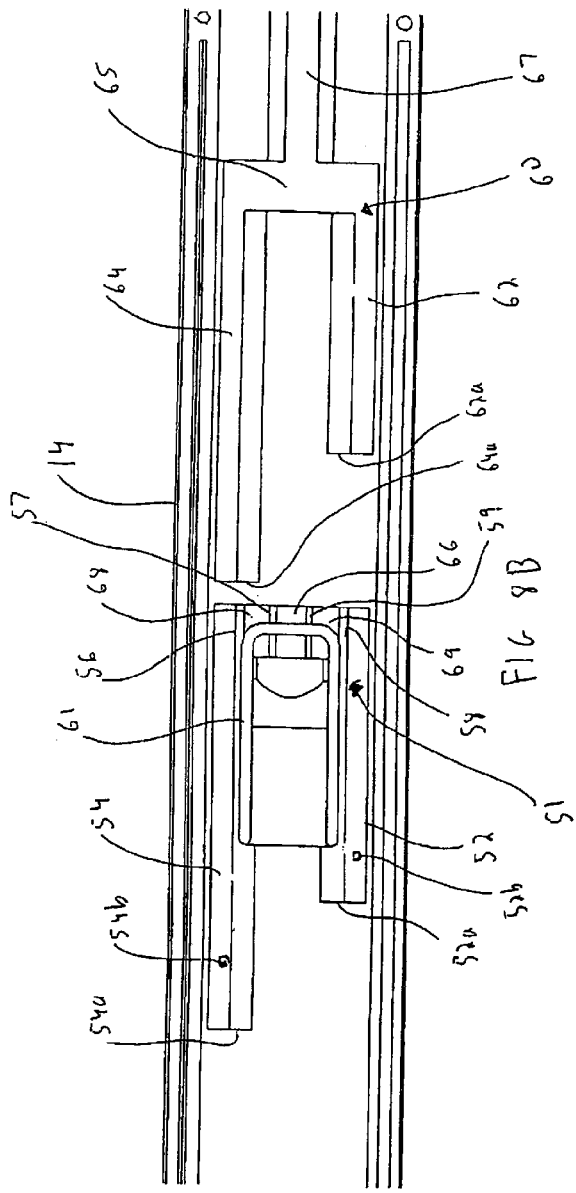

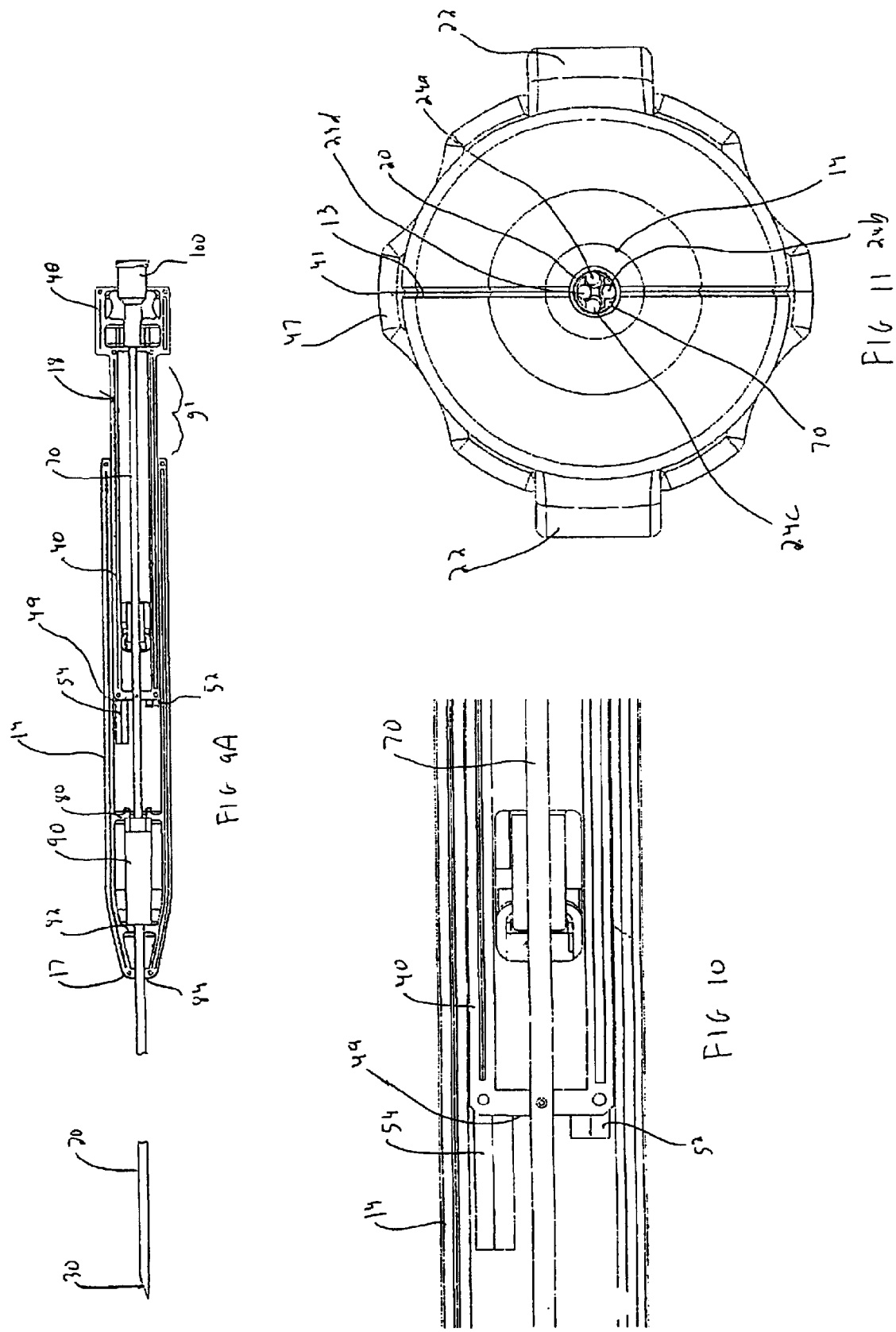

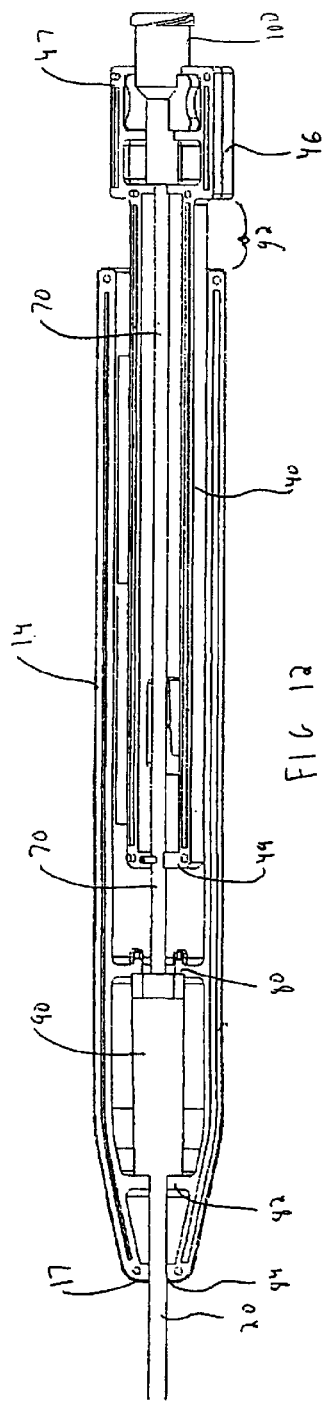

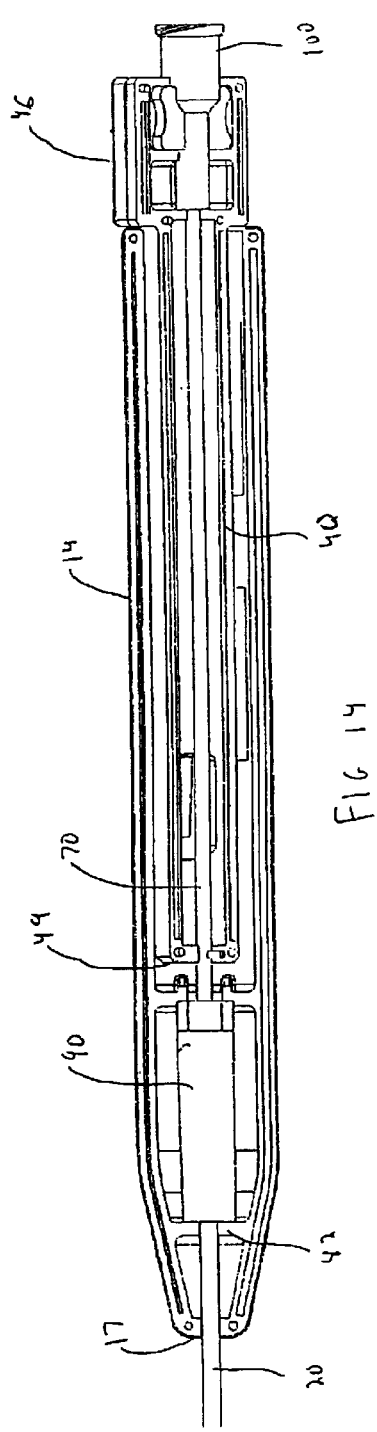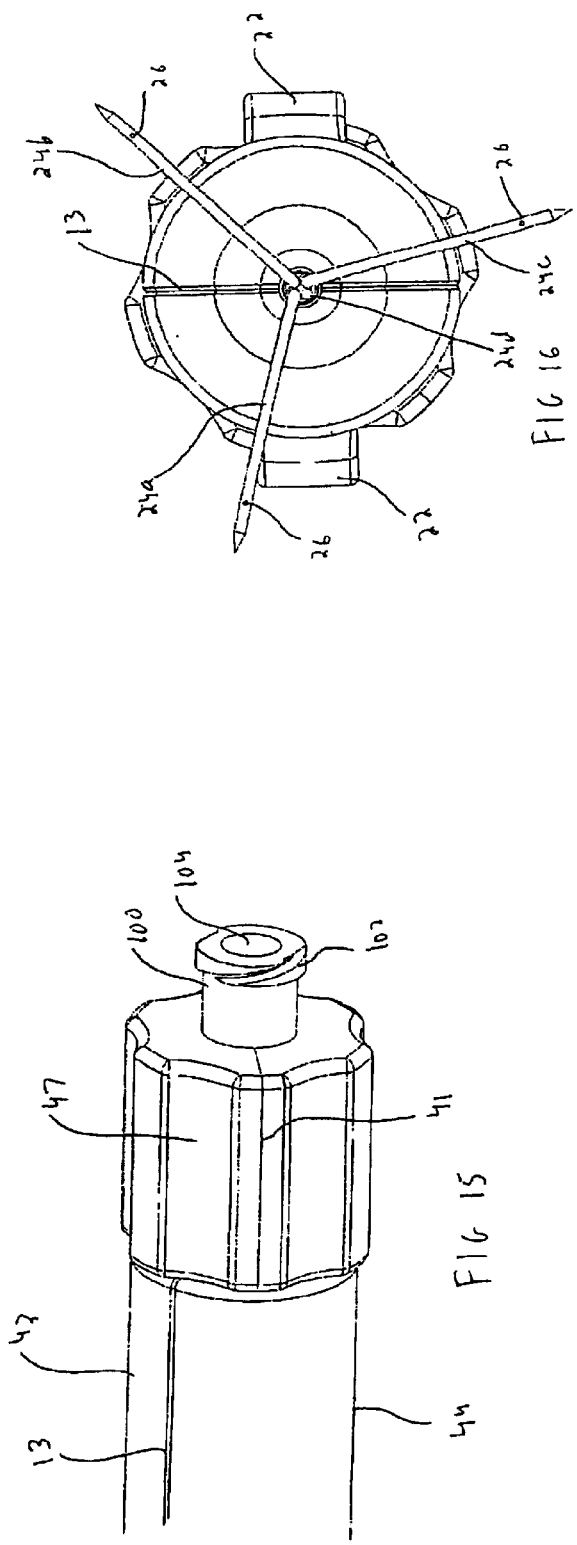

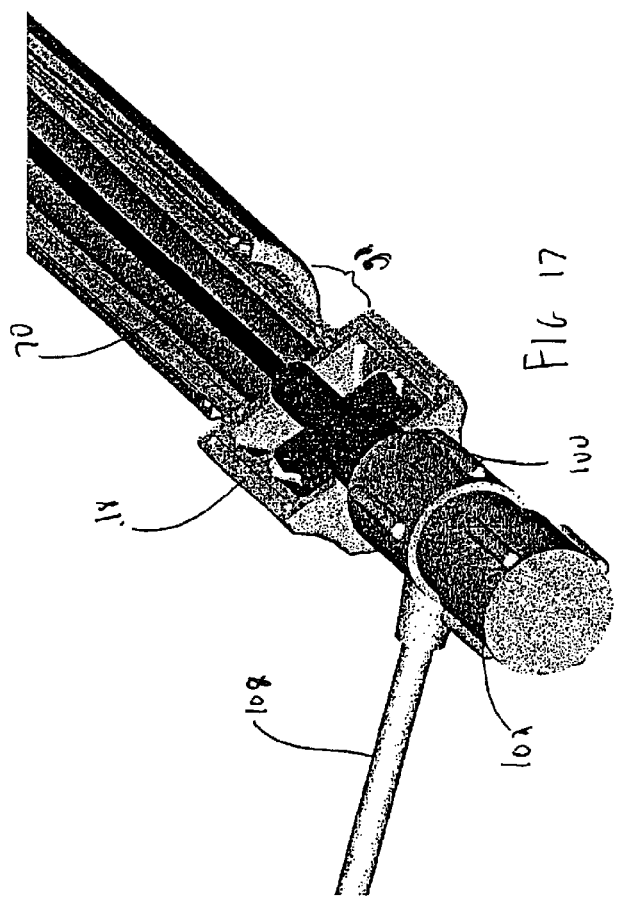
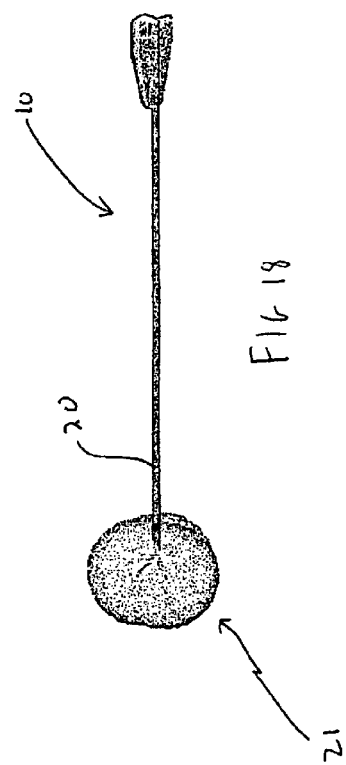

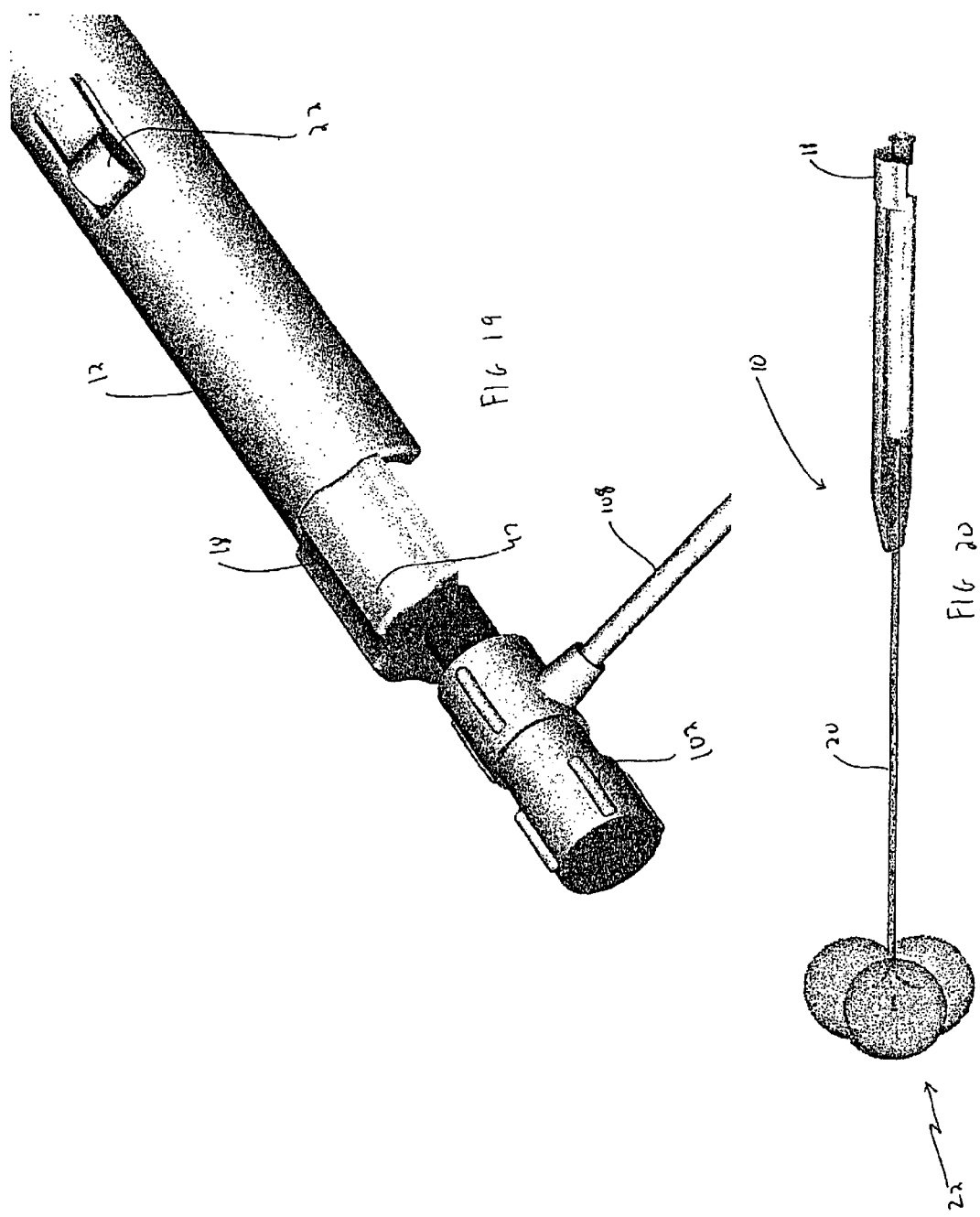

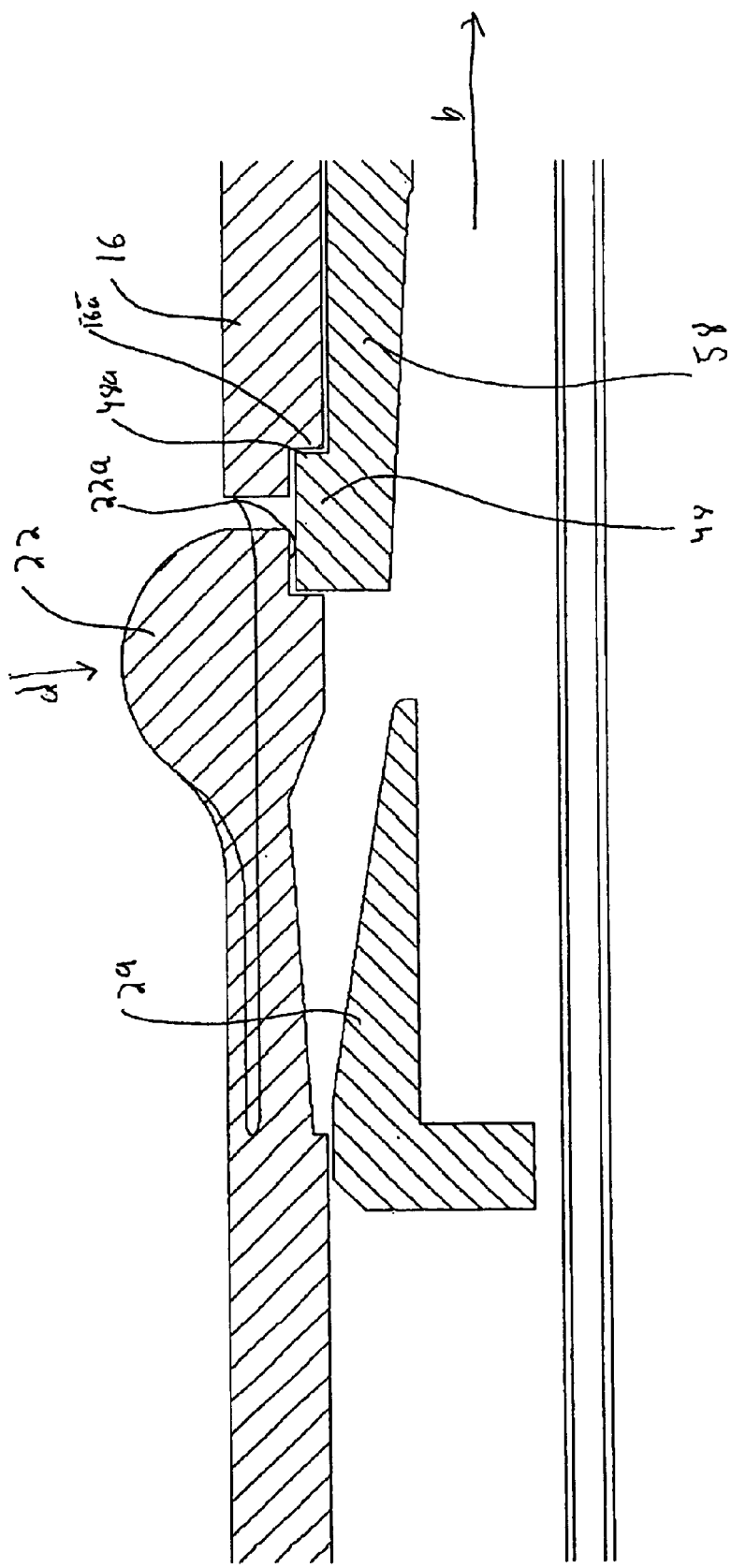

APPARATUS FOR DELIVERING ABLATION FLUID TO TREAT LESIONS

BACKGROUND

This application claims priority from provisional application No. 60/272,119, filed Feb. 28, 2001, the entire contents of which is incorporated herein by reference.

TECHNICAL FIELD

This application relates to a surgical apparatus for treating lesions and more particularly to an apparatus that delivers ablation fluid such as ethanol or acetic acid to ablate lesions.

BACKGROUND OF RELATED ART

One current method of treating hepatic (liver) cellular carcinomas is using electrosurgical energy in the form of radiofrequency energy. A series of electrodes are placed in the malignant tumor and a generator is activated to apply energy to the electrodes which heats the tissue to destroy the tumor. One example of such device is marketed by RITA Medical Systems which has an array of electrodes, offered in various configurations, which are curved outwardly from the tube in which they are constrained. It has been documented however in the literature that RF energy application is not consistently sufficient to ablate the cancerous tissue. Therefore, the patient must repeatedly return to the physician for additional applications of RF energy until the lesion is satisfactorily ablated. This not only adds to the expense of the procedure but can have an adverse psychological impact on the patient whose treatment is prolonged and characterized by frequent hospital visits. In additional to the clinical disadvantage, utilization of RF energy can be expensive since capital equipment, i.e. an RF generator for applying and controlling the electrosurgical energy, is required.

Another method of treating tumors is the injection of alcohol through a needle to ablate the tumor. The alcohol is typically about 95% to 99.5% ethanol and diffuses into the cancerous cells to produce immediate necrosis due to effects of cellular dehydration and protein denaturation followed by small vessel thrombosis.

One instrument currently being utilized to deliver ethanol to treat hepatic tumors is the Bernardino infusion needle, marketed by Cook of Bloomington, Ind. The needle is hollow and has two infusion ports adjacent the sharp distal tip. This device, however, has several disadvantages. The ethanol is injected only adjacent the distal tip, creating a relatively small tumor treatment (ablation) zone. Therefore, the infusion needle must be repeatedly maneuvered and repositioned in various regions of the tumor and ethanol repeatedly injected until the entire region has been treated. In fact, oftentimes the needle will have to be fully removed and reinserted into the patient, sometimes as frequently as twenty times in a single surgical procedure thereby requiring twenty needle sticks, to ensure the entire region to be treated receives an adequate supply of ethanol.

It would therefore be desirable to provide a fluid injection needle with a larger treatment zone capability to ablate a larger tumor. This would avoid multiple needle sticks, reduce the time required for treatment, and simplify the surgical procedure. A more uniform treatment zone would also be desirable. It would also be advantageous if the treatment zone can be varied so that the same delivery needle can be adapted for different sized lesions. Such injection needle could advantageously be used to inject acetic acid, ethanol or other ablation fluids.

SUMMARY

The present invention overcomes the problems and deficiencies of the prior art by advantageously. The present provides a surgical apparatus for delivering fluid to treat a lesion comprising a housing, a hollow elongated member extending from the housing, and a plurality of tines positioned in the elongated member. Each of the tines has a lumen and at least one opening communicating with the lumen for delivering fluid to the lesion. An actuator is operatively associated with the plurality of tines and is actuable to a first position to move the plurality of tines from a retracted position substantially within the elongated member to a first deployed position extending from the elongated member and is actuable to a second position to move the plurality of tines from the first position to a second deployed position extending further from the elongated member. The plurality of tines are preferably retained in the first and second deployed positions by retention structure.

Preferably, the actuator is movable in a first direction to move the tines from the retracted position to the first deployed position and movable in a second different direction to move the tines from the retracted position to the second deployed position so the tines are advanced further from the elongated member. The actuator is preferably rotatable and axially slidable to move the tines from the retracted position to the first deployed position and from the retracted position to the second deployed position. The elongated member preferably comprises a needle with a penetrating distal end.

Preferably, the housing includes a first and second track formed in an inside wall of the housing and the actuator includes a plunger having a first projecting surface slidably movable within the first track and a second projecting surface sidably movable within the second track.

Preferably, the plurality of tines are composed of shape memory metal wherein one of tines is extendable in substantial alignment with a longitudinal axis of the elongated member and at least two of the tines are extendable at an angle to the longitudinal axis of the elongated member, preferably up to about 90 degrees. The tines can alternatively be composed of stainless steel.

In a preferred embodiment, the retention structure comprises a first detent located in the first track enagagable by the plunger to retain the tines in the first deployed position and a second detent located in the second track engagable by the plunger to retain the tines in the second deployed position.

The present invention also provides a surgical apparatus for delivering fluid to treat a lesion comprising a housing, an elongated tissue penetrating member extending from the housing, and first and second tines positioned in the elongated member. Each of the tines has a lumen and at least one opening communicating with the lumen for delivering fluid to the lesion wherein the first and second tines are movable between a retracted position, a first deployed position and a second deployed position. The first tine is substantially aligned with a longitudinal axis of the elongated member in the retracted position and in the first deployed position, and the second tine is substantially aligned with a longitudinal axis of the elongated member in the retracted position and at an angle to the longitudinal axis of the elongated member in the first deployed position.

An actuator is preferably provided which is rotatable in a first direction and axially slidable to move the first and second tines to the first deployed position and rotatable in a second direction and axially slidable to move the first and second tines to the second deployed position. The housing preferably includes a short track and a long track wherein the actuator is slidable in the short track to move the first and second tines to the first deployed position and slidable in the long track to move the first and second tines to the second deployed position. The actuator in the preferred embodiment comprises a plunger having a projecting surface slidably engageable within either the short or long track as the first and second tines are moved to the deployed positions.

The present invention also provides an apparatus for delivering fluid to treat a lesion comprising a housing, an elongated member extending from the housing, a plurality of tines positioned in the elongated member, each having a lumen and at least one opening communicating with the lumen for delivering fluid to the lesion, and an actuator operatively associated with the tines. The actuator is actuable to a first position to move the plurality of tines from a retracted position substantially within the elongated member to a first deployed position extending distally of the elongated member and actuable to a second position to move the plurality of tines from the retracted position to a second deployed position extending distally of the elongated member, wherein the actuator is movable to the second position without movement to the first position.

The present invention also provides an apparatus for delivering fluid to treat tumors comprising a housing, an elongated member extending from the housing, a plurality of tines positioned in the elongated member, each having a lumen and at least one opening communicating with the lumen for delivering fluid to the lesion, and a release mechanism operatively associated with the plurality of tines operable to release the plurality of tines from the elongated member to enable withdrawal from the apparatus. An actuator is operatively associated with the tines, the actuator actuable to move the plurality of tines from a first position substantially within the elongated member to a deployed position extending from the elongated member.

An elongated support is preferably connected to the tines and connected to the actuator, wherein the elongated support and the actuator are removable with the tines from the elongated member and the housing. The housing may also include a release lever engagable with a tab extending from the actuator, the release lever biasing the tab out of engagement to enable release of the actuator. Preferably a collagen plug deployer is insertable into the elongated member after release and removal of the elongated support, actuator and plurality of tines.

A method for treating a lesion is also provided comprising:

inserting an apparatus adjacent the lesion;

rotating an actuator in a first direction and advancing the actuator in a distal direction to deploy a plurality of tines from the apparatus; and injecting ablation fluid through a plurality of openings in the tines to ablate the lesion.

BRIEF DESCRIPTION OF THE DRAWINGS

Preferred embodiment(s) of the present disclosure are described herein with reference to the drawings wherein:

FIGS. 4 and 5 are enlarged perspective views (at different angles) of the distal portion of the apparatus of FIG. 1 showing the tines in a second deployed position to define a second treatment zone;

FIG. 7 is an enlarged exploded view of the apparatus of FIG. 1 showing the housing halves for retaining the needle and needle sleeve;

FIG. 8A is an enlarged perspective view of the second plunger half showing the engagement tab and projection;

FIG. 8B is a side view of the first housing half showing the tracks for receiving the engagement tab and projection of the first plunger half;

FIG. 8C is a perspective view of the housing half of FIG. 8B;

FIG. 9A is a side view of the apparatus of FIG. 1 with the second housing half and the second plunger half removed to illustrate the position of the mounting tube and first plunger half when the apparatus is in the initial position with the tines retracted within the needle;

FIG. 10 is an enlarged side view illustrating the first plunger half in the initial position within the first housing half;

FIG. 11 is an enlarged front view of the apparatus in the initial position of FIG. 9A;

FIG. 12 is a side view of the apparatus with the second housing half and second plunger half removed to illustrate the position of the first plunger half when the apparatus is in the intermediate position with the tines partially deployed from the needle to a first deployed position;

FIG. 13 is an enlarged front view of the apparatus in the intermediate position of FIG. 12;

FIG. 14 is a side view of the apparatus with the second housing half and second plunger half removed to illustrate the position of the first plunger half when the apparatus is in the advanced position with the tines fully deployed from the needle to a second deployed position;

FIG. 15 is an enlarged view of the proximal end of the apparatus of FIG. 14 showing the plunger knob rotated and linearly advanced for full deployment of the tines;

FIG. 16 is an enlarged front view of the apparatus in the advanced position of FIG. 14;

FIG. 17 is a perspective view of the proximal portion of the apparatus showing the plunger rotated and axially advanced to an intermediate position to deploy the tines to the first deployed position;

FIG. 18 is a side view showing a first zone of treatment, depicted schematically by spherical zones, for the first deployed position of the tines;

FIG. 19 is a perspective view of the proximal portion of the apparatus showing the plunger rotated and axially advanced to the advanced position to fully deploy the tines to the second deployed position;

FIG. 20 is a side view showing a second zone of treatment, depicted schematically by spherical zones, for the second deployed position of the tines;

FIG. 21 is an enlarged cross-sectional view showing the interaction of the release lever and finger to release the plunger to enable withdrawal of the tines, mounting tube and plunger from the needle and housing.

DETAILED DESCRIPTION OF PREFERRED EMBODIMENTS

Figure 1:
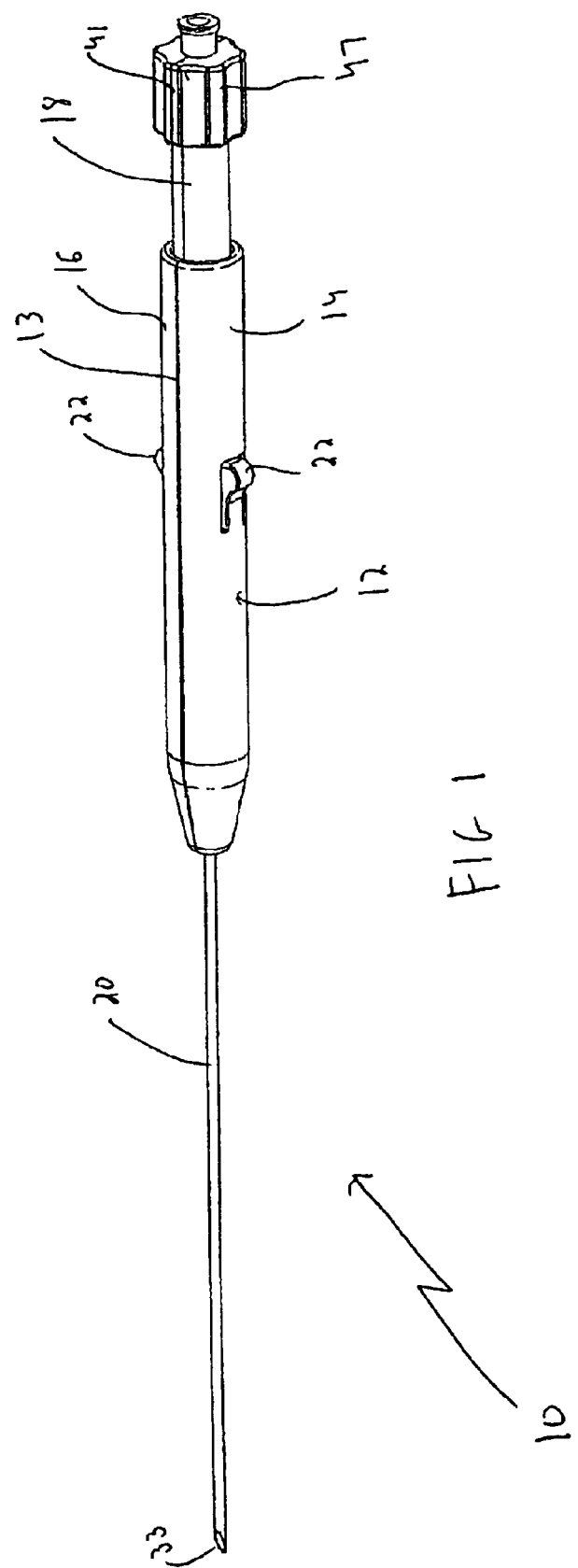
FIG. 1 is a perspective view of the apparatus of the present invention in the initial position with the tines fully retracted within the needle.

Referring now in detail to the drawings where like reference numerals identify similar or like components throughout the several views, the apparatus of the present invention for delivering ethanol or other ablation fluid for tumor ablation is designated generally by reference numeral 10 and illustrated in FIG. 1. Apparatus 10 includes a housing or body 12 composed of housing halves 14, 16, an actuator 18, and an elongated tubular member or needle 20 extending distally from the housing 12. Within the needle 20 are positioned a plurality of tines which are extendable from the needle 20 in response to movement of the actuator 18. The tines contain openings for delivery of the ablation fluid to the target tissue. Release levers 22 on housing 12 operate to release the tines from the apparatus 10 in the manner described below.

Figure 2:
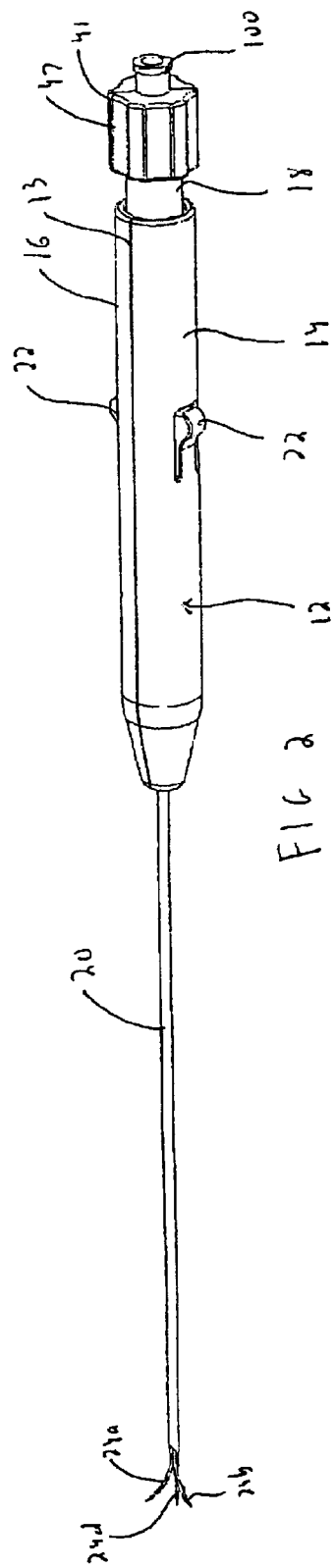
FIG. 2 is a perspective view of the apparatus of FIG. 1 with the tines in a first deployed position to define a first treatment zone.
Figure 3:
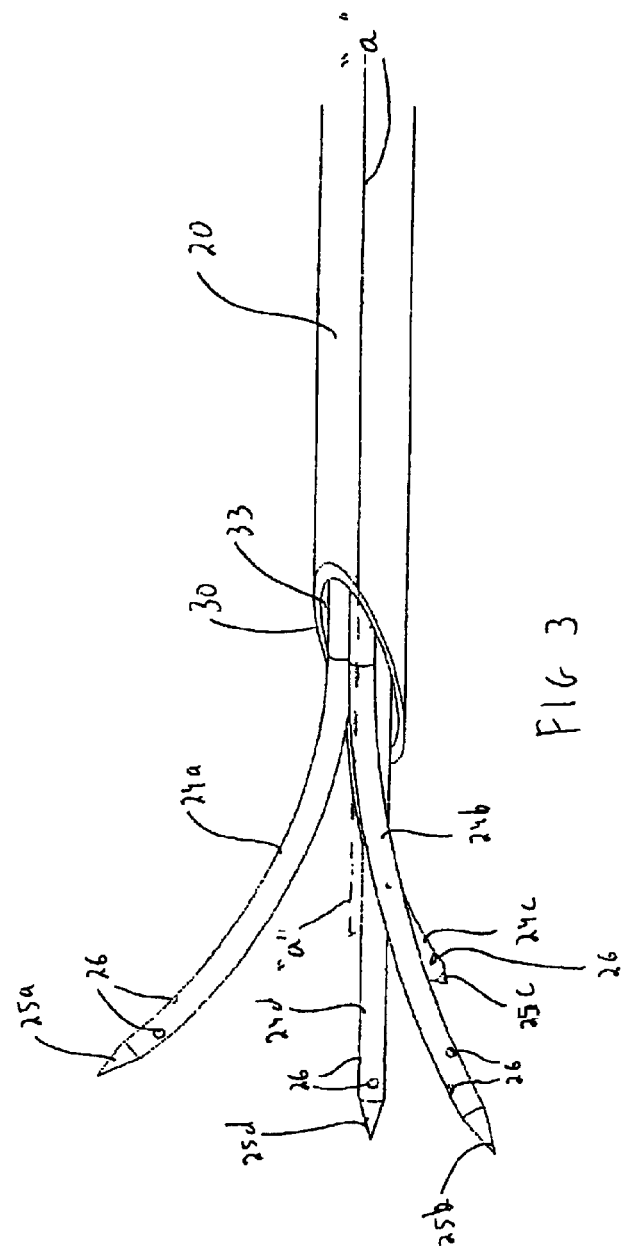
FIG. 3 is an enlarged perspective view of the distal portion of the apparatus of FIG. 2 showing the tines in the first deployed position.

FIG. 1 illustrates the tines in the retracted or non-deployed position with the actuator 18 in its initial (neutral) position. FIGS. 2 and 3 illustrate the tines, designated by reference numerals 24a–24d, in a first deployed (or intermediate) position. As can be appreciated, actuator 18, which is in the form of a plunger with a knurled grip 47, is rotated and slid axially in a distal direction towards the housing 12. This advances tines 24a–24d through the distal opening 33 of needle 20, enabling the tines to extend angularly with respect to the longitudinal axis "a" of the needle 20 as shown. Each of the tines 24a, 24b, 24c and 24d has a respective penetrating tip 25a–25d and a series of openings 26 for delivering fluid, e.g. ethanol or acetic acid, to the tissue. The beveled distal end 30 of needle 20 forms a cutting edge to facilitate passage of the apparatus 10 through the tissue when the tines 24a–24d are in the retracted position.

FIGS. 4 and 5 illustrate the tines 24a–24d in a second or fully deployed position. In this position, the actuator 18 has been rotated in the opposite direction to that of FIG. 2 and slid axially distally towards the housing 12 a greater distance than in FIG. 2. This deploys the tines 24a–24d further from the distal end 30 of the needle 20, and at a greater angle to the longitudinal axis "a" of the needle 20, providing a larger tissue treatment zone as will be described in detail below.

The structural components of the apparatus 10 will now be described with reference to the exploded views of FIG. 6 and 7. Actuator or plunger 18 is composed of first and second halves 40, 42 which are identical in configuration. Actuator or plunger half 40 has a proximal region 44, which has a depression 46 cooperating with a corresponding depression formed in proximal region 43 of plunger (actuator) half 42 to form a mount for luer fitting 100. Plunger half 42 has an engagement tab 48 formed on flexible finger 58 and a projection 50 spaced proximally from the engagement tab 48, both extending outwardly from the outer surface and designed to engage a track in the first housing half 16 described below. Flexible finger 58 is formed by cutout 61 formed in plunger half 42. Ledge 48a (FIG. 8A) of tab 48 limits proximal movement of the plunger half 42 in the manner described below. Likewise, plunger half 40 has an identical flexible finger having an engagement tab 55 and a projection 45 (shown in phantom) designed to travel in a track formed in second housing half 14. Note the terms "first" and "second" as used herein to describe the plunger and housing halves are solely for the purpose of clarity and convenience.

Figure 6:
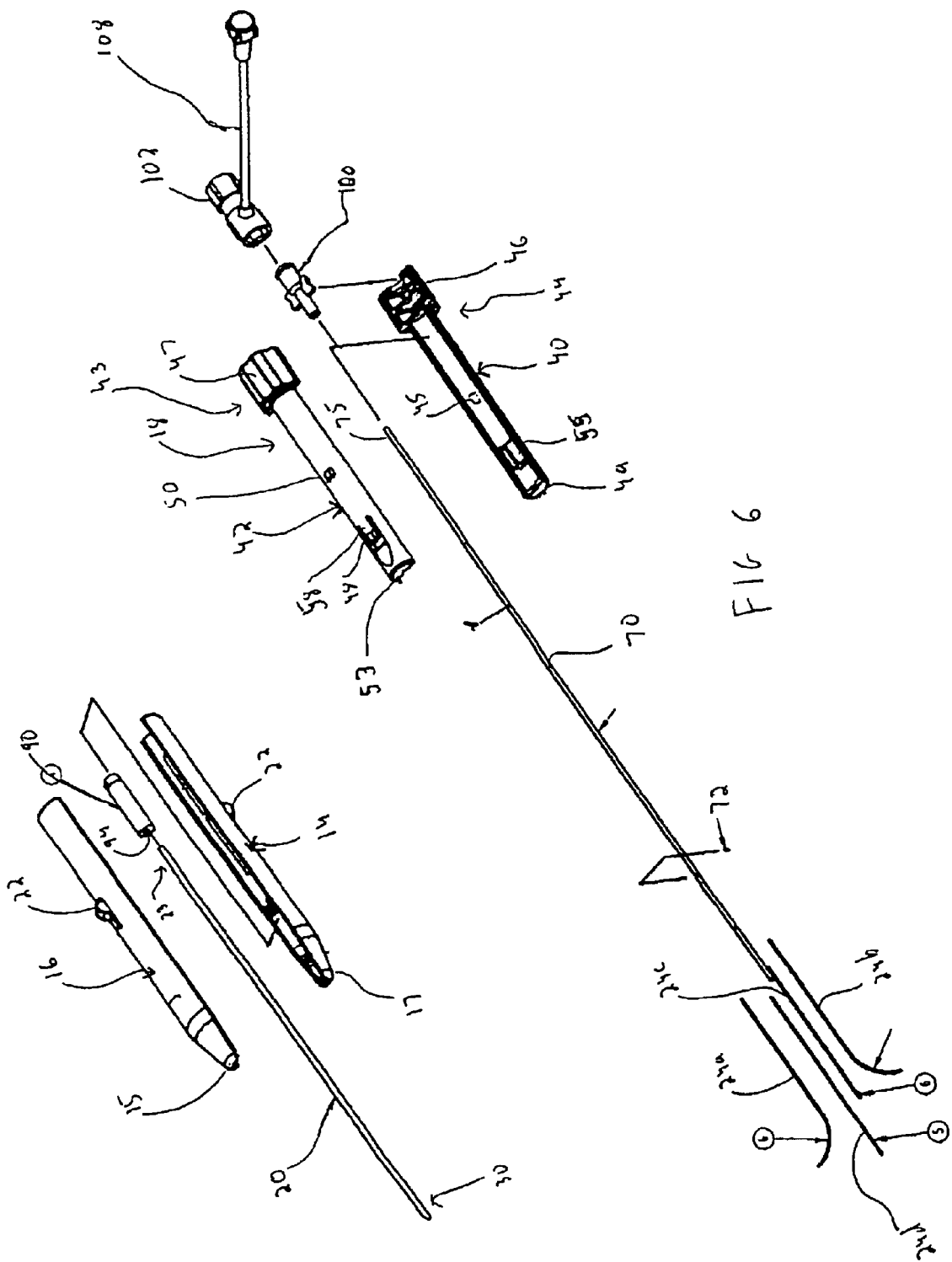
FIG. 6 is an exploded view of the apparatus of FIG. 1.

With reference to FIGS. 6 and 7, mounted within plunger 18 is an elongated mounting tube 70 having an internal lumen extending along its length. The proximal end 75 of mounting tube 70 is connected to luer fitting 100 to enable fluid flow therethrough. Mounting tube 70 extends through the lumen of needle sleeve 90 and needle 20, terminating adjacent the distal end 30 of needle 20. Tines 24a–24d are connected to mounting tube 70 by mounting pin 72 and mounting tube 70 is connected to plunger 18 by pin 74. Consequently, rotation and axial movement (advancement/retraction) of plunger 18 rotates and moves the mounting tube 70 axially, which in turn rotates and moves the connected tines 24a–24d axially. Mounting pin 72 is dimensioned so that its diameter is of sufficient size to prevent proximal movement of the tines in mounting tube 70, but is less than the diameter of the internal lumen of mounting tube 70. This enables ethanol (or other ablation fluid) to flow around the mounting pin 72 and through the tines 24a–24d for delivery to the patient.

As noted above, housing 12 is composed of first and second housing halves 14 and 16 which are identical in configuration. Only housing half 14 will be described and identified with reference numerals, it being understood that housing half 16 has the identical structure.

Housing half 14 has two sets of mounting ribs 80, 82 which cooperate with identical ribs (not shown) on housing half 16 to frictionally engage and retain needle sleeve 90 and needle 20, respectively. More specifically, needle sleeve 90 is seated within ribs 80, has an axial opening 95 formed therethrough to accommodate fluid flow, and has a flat surface 92 to prevent rotation of the needle 20 within the housing 12. Needle sleeve 90 terminates proximally of ribs 82 (see also FIG. 9A) where distal opening 94 receives a proximal portion 23 of the needle 20 which can be bonded or attached thereto by any conventional means. Needle 20 extends between ribs 82 and exits through distal slot 84, extending a sufficient distance distally of the distal ends 15, 17 of housing halves 16, 14 to enable access to the surgical site. The needle sleeve 92 and needle 90 are mounted within the ribs of housing half 16 in the identical manner.

Each of the housing halves 14,16 has a distal track 51 and a proximal track 60 configured to receive the respective engagement tabs 48, 55 and projections 50, 45 of plunger halves 42, 44. It should be appreciated that although the track is shown integrally formed on the inside wall of the housing halves, it is also contemplated that a separate component containing the desired track configuration can be mounted to the housing halves to provide the necessary engagement with the plunger tabs and projections.

With reference to FIGS. 8B and 8C, distal track 50 has a short track 52 and long track 54 with a pocket 66 formed in between; proximal track 60 has a long track 64 and a short track 62 joined by connector track 65. Exit track 67 extends proximally from connector track 65 to enable removal of the plunger halves 42, 44 in the manner described below. The identical track configuration is formed on housing half 16 and is therefore not shown or labeled.

As noted above, actuator 18 is positioned within housing 12 for both rotational and sliding movement therein. More specifically, engagement tab 55 rides in the distal track 51 and projection 45 rides in the proximal track 60 of housing half 14. Similarly, engagement tab 48 and projection 50 travel in the respective distal and proximal tracks of housing half 16.

The movement of the engagement tab and projection within the track will now be described for convenience only with reference to the engagement tab 55 and projecting surface 45 of plunger half 40 within housing half 14, it being understood that the identical movement will occur of engagement tab 48 and projection 50 of plunger half 42 within housing half 16.

In the initial position of plunger 18, projection 45 is seated in connector track 65 of track 60 and engagement tab 55 is seated in pocket 66 of track 51 with ledge 48a abutting wall 25 preventing proximal movement thereof. When plunger 18 is rotated in a clockwise direction, engagement tab 55 rides over ramp 59, and down ramp 58 into short track 52, providing a tactile feel to the user that the plunger has been rotated so that the tab can engage short track 52 for movement of the tines to the first (intermediate) deployed position. This clockwise rotation of plunger 18 also moves projection 45 along transverse connector track 65 and in alignment with short track 62. The plunger 18 is then pushed inwardly toward the housing 12. The axial movement of the plunger 18 enables engagement tab 55 to travel distally within short track 52 and projection 45 to travel distally within short track 62. Travel continues until the engagement tab 55 and projection 45 contact distal walls or stop 52a and 62a of short tracks 52, 62, respectively. Detent 52b formed on short track 52 limits proximal movement of tab 55 in short track 52a to prevent unwanted retraction of plunger 18. This distal movement of plunger 18 advances mounting tube 70 distally with respect to needle 20 so tines 24a–24d advance from the needle 20 to the first deployed (intermediate) position of FIGS. 12 and 13.

When plunger 18 is rotated counterclockwise from the neutral (initial) position, engagement tab 55 is moved from pocket 66, over ramp 57 and down ramp 56 into long track 54 while projection 45 moves along connector track 65 into long track 64. This movement over ramp 57 provides a tactile feel to the user that the plunger has been rotated. Plunger 18 is pushed distally and the tab 55 and projection 45 travel distally within long tracks 54, 64 respectively, until contacting distal walls 54a, 64a which act as a stop to limit distal movement. This axial movement of plunger 18 moves mounting tube 70 distally a further distance than travel within short tracks 52,62, causing ejection of the tines from needle 20 to a second or fully deployed position of FIGS. 14 and 16. In the second deployed position, preferably the tines 24a–24d are at an angle of about 90 degrees with respect to the longitudinal axis of the elongated needle 20, although other angles are also contemplated. In this second position, detent 54b in long track 54 restricts proximal movement of tab 55, preventing unwanted retraction of plunger 18. Detents 52b and 54b are preferably slightly angled to facilitate advancement of tabs 55 and 48 over the detents, but restrict retraction unless a sufficient force is applied.

On knurled grip 47 is an alignment surface 41 which in cooperation with alignment seam 13 of housing 12 (see FIGS. 1, 2 and 15) provides a visual indication to the user of the rotational position of the plunger 18 and therefore an indication of the position of the tines 24a–24d. More specifically, in the first and second deployed positions, alignment surface 41 is out of alignment with alignment seam 13 of housing 12 (see e.g. FIG. 15), indicating to the user that the tines 24a, 24d are deployed.

Figure 9B:
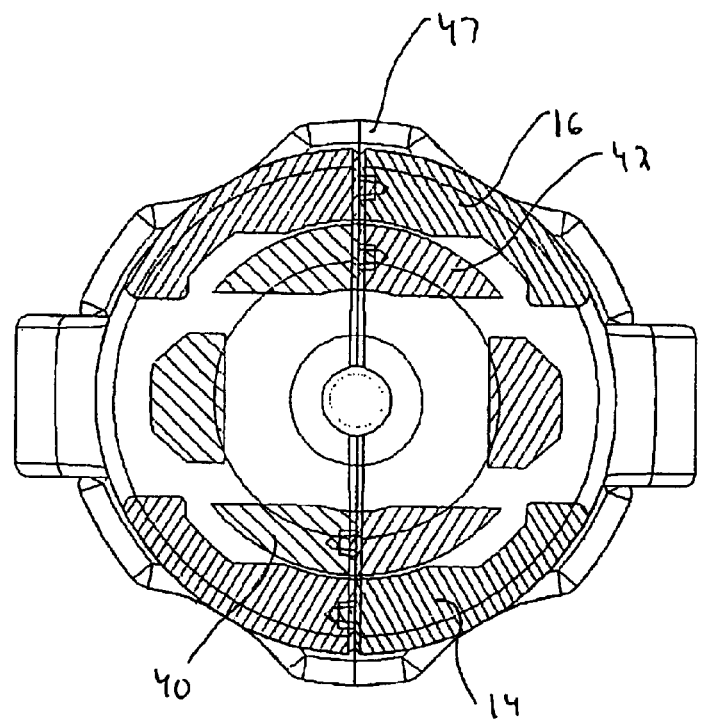
FIG. 9B is a transverse cross-sectional view showing the interaction of the plunger and housing halves (the tines, tube and needle removed for clarity) when the apparatus is in the initial position of FIG. 1.
Figure 9C:
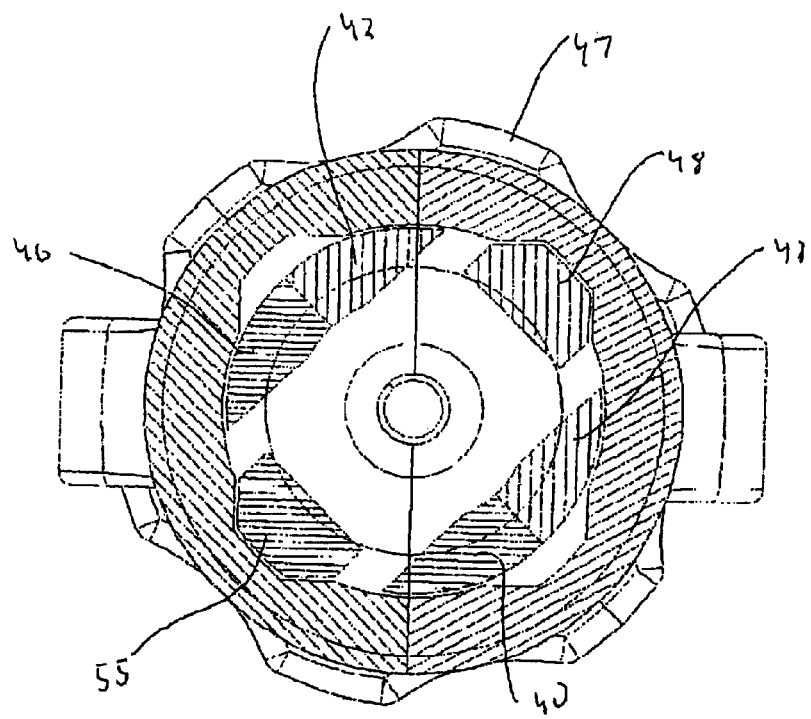
FIG. 9C is a transverse cross-sectional view showing the interaction of the plunger and housing halves (the tines, tube and needle removed for clarity) when the apparatus is in the second (fully) deployed position.

Note that in the first initial position knurled grip 47 is spaced a distance or gap "g1", shown in FIG. 9A, from the proximal end of housing 12. In the first deployed position, shown in FIG. 12, the distance between the proximal edge of housing 12 and the knurled grip 47 is defined by a smaller gap, namely gap g2. In the second deployed position, knurled grip 47 abuts the proximal edge of housing 12. (see FIG. 15)

In use, the apparatus 10 is inserted percutaneously through the skin to the target tissue site with the beveled edge 30 of needle 20 penetrating through tissue. The apparatus 10 is inserted with actuator 18 in the initial or neutral position so that tines 24a–24 are fully retracted inside needle 20. Once adjacent the target lesion, the surgeon has the option to rotate the actuator 18 in a clockwise direction to create a first treatment zone or rotate the actuator in the opposite (counterclockwise) direction to create a second, larger treatment zone.

If a smaller treatment zone is desired, actuator 18 is rotated clockwise and then pushed axially inwardly, with the engagement tabs and projection on the plunger halves riding in the short track portions of the distal and proximal tracks. This deploys the tines 24a–24d to the position of FIGS. 2 and 3 with the tips 25a–25d penetrating tissue. Note that alignment surface 41 is out of alignment with seam 13, indicating to the user that the plunger has been moved from its neutral position. Next, ethanol (or other ablation fluid) is injected through tube 108 of a conventional touhy borst 102 which is threadedly attached to luer fitting 100, transported through the lumen 104 in luer fitting 100 and through mounting tube 70 and through the lumens in tines 24a–24, exiting through holes 26. Note that although two holes are shown in each tine 24, it is contemplated that one hole or more than two holes can be provided on various portions of one or more of the tines communicating with the internal lumen to achieve the desired effect. In this first deployed position, tine 24d remains in a straight position substantially aligned with the longitudinal axis "a" of the needle 20, and the other three tines 24a, 24b and 24c extend outwardly at an angle to the longitudinal axis "a", as they return to their memorized configuration to create a treatment zone Z1 (FIG. 18).

Figure 6A:
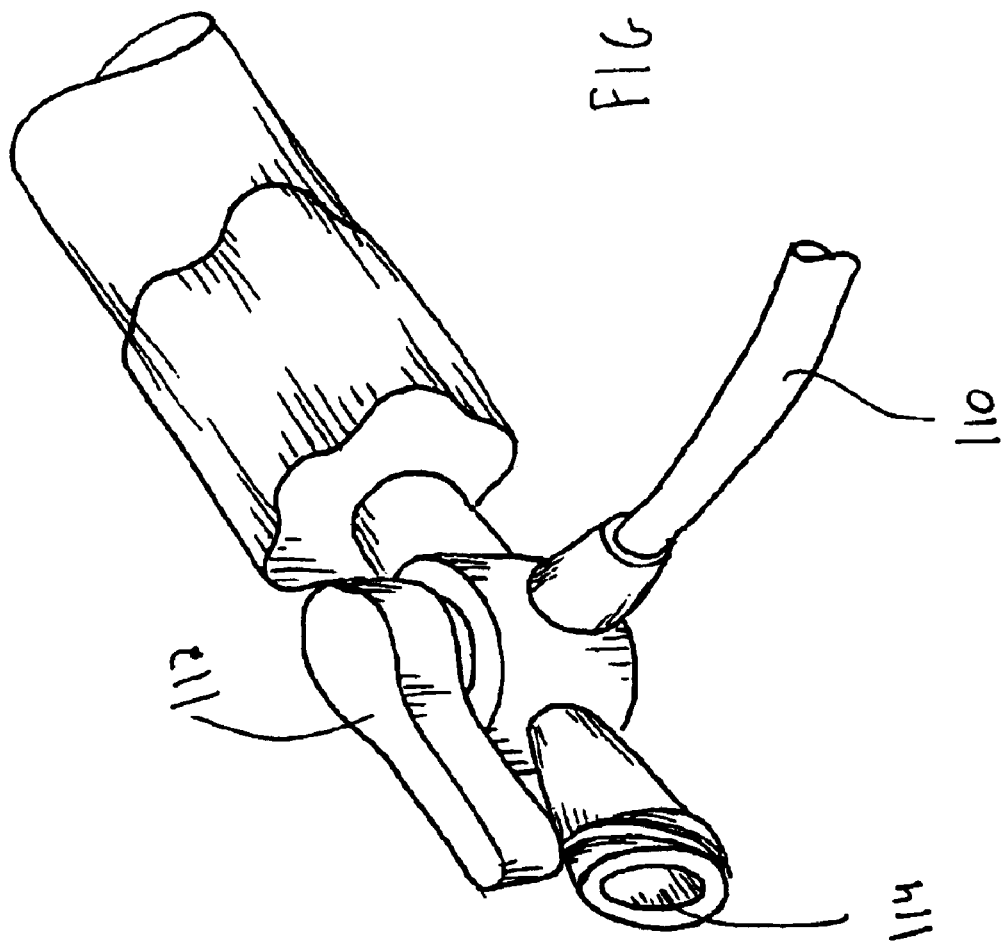
FIG. 6A is a perspective view of a three way stopcock.

Note that to facilitate passage of the tines 24a–24d through needle 20 and into the tissue, cold saline is injected through the tines 24a–24d in their retracted position within needle 20. Tines 24a–24d are preferably composed of shape memory metal, such as Nitinol, a nickel titanium alloy, which characteristically exhibits rigidity in the austenitic state and more flexibility in the martensitic state. The cold saline maintains the temperature dependent tines 24a–24d in a relatively softer condition as they are in a martensitic state within needle 20. This facilitates their exit from the needle as frictional contact between the tips 25a–25d of the tines 24a–24d and the inner wall of the needle would otherwise occur if the tines were maintained in a rigid condition. After deployment, i.e. advancement from needle 20, the tines 24a–24d are exposed to the warmer body temperature. This change in temperature causes the tines 24a–24d to achieve their desired degree of rigidity as they transition to their austenitic state to facilitate passage through the tissue. Their warming thus enables them to return to their memorized configuration at an angle to the longitudinal axis of needle 20. The three way stopcock of FIG. 6A enables ethanol (or other ablation fluid such as acetic acid) to be inserted through tube 110 when stopcock 112 is in a first position, allows cold saline to be inserted through opening 114 when stopcock 112 is in a second position (rotated 90 degrees with respect to the first position), and prevents fluid flow when the stopcock is in the third position.

As shown in FIG. 18, in the first deployed position, due to the deployed configuration of the tines and the placement of the exit holes 26, the portion of the lesion that is ablated by the ethanol is defined by the four intersecting spheres designated "Z1".

To create a larger treatment zone, the actuator 18 is rotated in a counterclockwise direction from its neutral position, and pushed inwardly so that tabs 48, 55 and projections 50, 45 of the plunger ride in the long track portions of the distal and proximal tracks 51, 60. This deploys the tines to the position of FIGS. 4, 5, and 16 as they are advanced from the needle 20 and exposed to warmer body temperature to return to their memorized configuration as they transition from the martensitic to the austenitic state.

Note that alignment surface 41 is out of alignment with seam 13 indicating that the actuator 18 has been rotated from its initial position. In this position, the tines 24a–24c extend at a greater angle with respect to the longitudinal axis of the needle 20 and a greater angle with respect to the straight tine 24d. Thus, when ethanol is injected through the tines 24a–24d, four intersecting spherical areas (FIG. 20) are created. As shown, these spheres occupy a larger area than the spheres of FIG. 18 to create a larger treatment zone Z2. Similar zones can be created with acetic acid or other ablation fluid.

If desired, the user can rotate the entire apparatus, or reposition the apparatus 10 to apply ablation fluid to create an even larger treatment zone or to fill in the zone between the four spherical areas Z1 or Z2.

Obviously, it is also contemplated that the orientations can be reversed so that clockwise rotation moves the tabs into the larger track to create a larger treatment zone and counterclockwise rotation is designed to create a smaller treatment zone.

Figure 22:
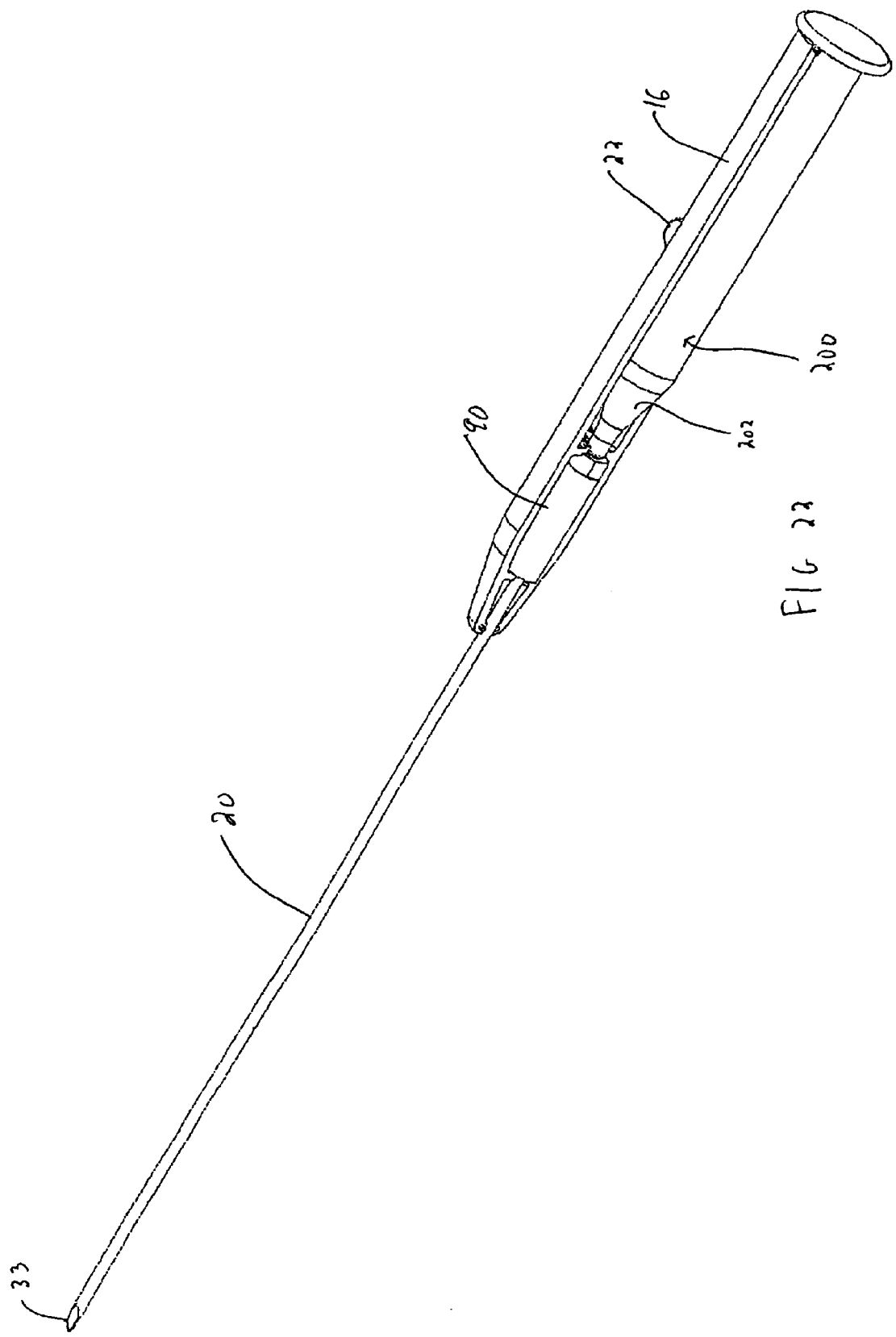
FIG. 22 is a perspective view of the apparatus of FIG. 1, with the second housing half removed to show the collagen plug deployer positioned within the apparatus.

After the lesion has been treated, it may be desired to insert a collagen plug. This plug functions to fill the hole left in the ablated tissue, e.g. the liver, to fill the void to prevent bleeding or leaking. The apparatus 10 of the present invention can be utilized to insert the plug by removing the plunger 18, mounting tube 70 and associated tines 24a–24d, and inserting a collagen plug deployer such as deployer 200 illustrated in FIG. 22. To release these components from the housing 12, the release levers on housing halves 14 and 16 are depressed, thereby disengaging the engagement tabs 48, 55.

More specifically, and with reference to FIG. 21, release of only one of the tabs will be described, namely tab 48 of plunger half 42, since tab 55 of plunger half 40 will be released by release lever 22 of housing half 14 in an identical manner. As shown in FIG. 21, the bottom surface of release lever 22 has a cutout 22a dimensioned to receive engagement tab 48. Ledge 48a of engagement tab 48 abuts wall 16a of housing half 16. When lever 22 is depressed in the direction of arrow "d", tab 48 is forced downwardly to disengage ledge 48a from wall 16a, thereby freeing plunger half 42 for proximal movement in the direction of arrow "b" for withdrawal from the instrument. Projections 45 and 50 slide in their respective exit tracks, e.g. exit track 67. Ramp 29 on plunger 42 provides a stop to limit downward movement of lever 22.

Once plunger 18 is removed, a collagen deployer 200 can be inserted into housing 12. Collagen deployer 200 has an elongated tube extending from housing 202 which is inserted through needle sleeve 90 and needle 20, terminating adjacent distal end 33. Positioned within the tube is a conventional cylindrically shaped collagen plug. A plunger is advanced towards the housing 202, contacting the proximal end of the collagen plug and forcing it distally out of the elongated tube of the deployer 200 and exiting distal end 33 of needle 20.

To facilitate locating the needle if rotation is desired, a skin patch such as that shown in FIG. 25 of commonly assigned co-pending provisional patent application filed Nov. 7, 2001 under Express Mail No. ET715467283 (incorporated herein by reference in its entirety) can be provided with alignment markings, preferably spaced about 60 degrees apart. The skin patch is preferably mounted to the skin by adhesive and has an opening to allow passage of the apparatus therethrough. The apparatus can include an orientation arrow to provide a visual alignment indicator with the markings of skin patch. By orienting the arrow in alignment with the skin patch markings, the user can better control 60 degree (or other variations) rotational changes of the apparatus as the marking will indicate the radial orientation of the tines.

It is contemplated that the apparatus 10 and 300 of the present invention injects alcohol or acetic acid into the tumor to ablate the tumor. The alcohol is typically about 95% to 99.5% ethanol and diffuses into the cancerous cells, to produce immediate necrosis due to effects of cellular dehydration and protein denaturation followed by small vessel thrombosis. Acetic acid requires smaller volumes than ethanol to treat the lesion. Acetic acid diffuses into the cancerous cells, burning through the tumor septi, i.e. the compartments within the tumor, to produce immediate necrosis due to effects of cellular dehydration and protein denaturation followed by small vessel thrombosis. The volume of the fluid and the number of in infusions can vary. It is also contemplated that the apparatus 10 and 300 of the present invention can be used to deliver other fluids such as hot saline or acid to ablate the tissue. Also, although contemplated for treating hepatic (liver) tumors, it is also contemplated that the apparatus 10 and 300 can be utilized to treat tumors in other regions of the body such as the spleen, pancreas, or brain. The apparatus can also be used to inject other fluids, e.g. therapeutic fluids such as chemotherapeutic agents or gene cells.

While the above description contains many specifics, those specifics should not be construed as limitations on the scope of the disclosure, but merely as exemplifications of preferred embodiments thereof. For example, the tines can be alternatively be made of stainless steel. Those skilled in the art will envision many other possible variations that are within the scope and spirit of the disclosure as defined by the claims appended hereto.

What is claimed is:

1. A surgical apparatus for delivering fluid to treat a lesion comprising:
   a housing;
   a hollow elongated member extending from the housing;
   first and second tines positioned in the elongated member, each of the tines having a lumen and at least one opening communicating with the lumen for delivering fluid to the lesion, the first and second tines movable between a retracted position, a first deployed position and a second deployed position; and
   an actuator operatively associated with the tines, the actuator movable in a first direction to move the first and second tines from the retracted position to the first deployed position and movable in a second direction to move the first and second tines from the retracted position to the second deployed position, the second direction being different from the first direction, and in the second deployed position the first and second tines are advanced further from the elongated member than in the first deployed position.

2. The apparatus of claim 1, wherein the actuator is rotatable in the first direction for movement of the first and second tines to the first deployed position and rotatable in the second direction for movement of the first and second tines to the second deployed position.

3. The apparatus of claim 2, wherein the actuator is axially slidable to move the first and second tines to the first and second deployed positions.

4. The apparatus of claim 3, wherein the housing includes a short track and a long track, a portion of the actuator slidable in the short track to move the first and second tines to the first deployed position and slidable in the long track to move the first and second tines to the second deployed position.

5. The apparatus of claim 1, wherein the first and second tines in the deployed position extend at an angle to a longitudinal axis of the elongated member.

6. The apparatus of claim 5, further comprising a third tine having a lumen and an opening in fluid communication with the lumen for delivery of fluid to the lesion, the third tine movable between a retracted position, a first deployed position, and a second deployed position, wherein in the first and second deployed positions the third tine is substantially aligned with the longitudinal axis of the elongated member.

7. An apparatus for delivering fluid to treat tumors comprising:
   a housing;
   an elongated member extending from the housing;
   a plurality of tines positioned in the elongated member, each of the tines having a lumen and at least one opening communicating with the lumen for delivering fluid to the lesion; and
   an actuator operatively associated with the plurality of tines, the actuator actuable to a first position to move the plurality of tines from a retracted position substantially within the elongated member to a first deployed position extending distally of the elongated member and actuable to a second position to move the plurality of tines from the retracted position to a second deployed position extending distally of the elongated member, the actuator movable to the second position without passing through the first position.

8. A surgical apparatus for delivering fluid to treat a lesion comprising:
   a housing;
   a hollow elongated member extending from the housing;
   a plurality of tines positioned in the elongated member, each of the tines having a lumen and at least one opening communicating with the lumen for delivering fluid to the lesion;
   an actuator operatively associated with the tines, the actuator actuable to a first position to move the plurality of tines from a retracted position substantially within the elongated member to a first deployed position extending from the elongated member and actuable to a second position to move the plurality of tines from the first deployed position to a second deployed position extending further from the elongated member, and a first retention member retaining the tines in the first deployed position to deliver fluid to a first treatment zone and retaining the tines in a second deployed position to deliver fluid to a second treatment zone larger than the first treatment zone, the actuator being slidable in an axial direction to deploy the tines and the first retention member being disposed internal of the housing and interacting with the slidable actuator to retain the tines in the first and second deployed positions; and
   a second retention member disposed internal of the housing and radially spaced from the first retention member, wherein the second retention member interacts with the slidable actuator to retain the tines in the first and second deployed positions.

9. A surgical apparatus for delivering fluid to treat a lesion comprising:
   a housing;
   a hollow elongated member extending from the housing;
   a plurality of tines positioned in the elongated member, each of the tines having a lumen and at least one opening communicating with the lumen for delivering fluid to the lesion; and
   an actuator operatively associated with the tines, the actuator actuable to a first position to move the plurality of tines from a retracted position substantially within the elongated member to a first deployed position extending from the elongated member and actuable to a second position to move the plurality of tines from the first deployed position to a second deployed position extending further from the elongated member, and a retention member retaining the tines in the first deployed position to deliver fluid to a first treatment zone and retaining the tines in a second deployed position to deliver fluid to a second treatment zone larger than the first treatment zone, the actuator being slidable in an axial direction to deploy the tines and the retention member being disposed internal of the housing and interacting with the slidable actuator to retain the tines in the first and second deployed positions, wherein the actuator includes a flexible member formed by a cutout in a body of the actuator, the flexible member being engagable with the retention member.

10. An apparatus for delivering fluid for tumor ablation comprising:
    a housing;
    an elongated tissue penetrating member extending from the housing and non-removably connected thereto,
    first and second tines positioned in the elongated member, each of the tines having a penetrating tip, a lumen and at least one opening in a sidewall spaced from the tip communicating with the lumen for delivering fluid to the lesion to a first treatment zone and a second treatment zone, the first and second tines movable between a retracted position, a first deployed position and a second deployed position and being retained by a retention member in the first and second deployed positions for delivering fluid to the first and second treatment zones, the first tine being substantially aligned with a longitudinal axis of the elongated member in the retracted position and in the first deployed position, and the second tine being substantially aligned with a longitudinal axis of the elongated member in the retracted position and at an angle to the longitudinal axis of the elongated member in the first deployed position, an actuator operatively associated with the tines, the actuator movable to move the first and second tines from the retracted position to the first deployed position and movable to move the first and second tines from the retracted position to the second deployed position, a first retention member interacting with the actuator to retain the tines in the first deployed position and in the second deployed position; and a second retention member disposed internal of the housing and radially spaced from the first retention member, wherein the second retention member interacts with the slidable actuator to retain the tines in the first and second deployed positions.

* * * * *